United States Patent [19]

Strunk et al.

[11] 3,976,672
[45] Aug. 24, 1976

[54] (HYDROCARBYLPHENYLSULFONYL)ALKYLTRIMETHYLSTANNANES

[75] Inventors: Richard J. Strunk, Cheshire; Winchester Loomis Hubbard, Woodbridge, both of Conn.

[73] Assignee: Uniroyal Inc., New York, N.Y.

[22] Filed: Dec. 15, 1975

[21] Appl. No.: 641,060

Related U.S. Application Data

[63] Continuation-in-part of Ser. No. 536,679, Dec. 26, 1974, abandoned.

[52] U.S. Cl. ................................ 260/429.7; 71/97; 424/288
[51] Int. Cl.² ......................................... C07F 7/22
[58] Field of Search ................................ 260/429.7

[56] References Cited
UNITED STATES PATENTS

| | | | |
|---|---|---|---|
| 2,604,483 | 7/1952 | Mack et al. | 260/429.7 |
| 3,031,483 | 4/1962 | Koopmans | 260/429.7 |
| 3,206,489 | 9/1965 | Stamm et al. | 260/429.7 |
| 3,398,169 | 8/1968 | Neumann et al. | 260/429.7 |
| 3,725,446 | 4/1973 | Peterson | 260/429.7 |
| 3,784,580 | 1/1974 | Peterson | 260/429.7 |
| 3,794,670 | 2/1974 | Peterson | 260/429.7 |
| 3,808,264 | 4/1974 | Peterson | 260/429.7 |
| 3,850,970 | 11/1974 | Peterson | 260/429.7 |

FOREIGN PATENTS OR APPLICATIONS 966,813   8/1964   United Kingdom

OTHER PUBLICATIONS

Ayrey et al., J. Organometal Chem. 35 105–109 (1972).

*Primary Examiner*—Helen M. S. Sneed
*Attorney, Agent, or Firm*—Willard R. Sprowls

[57] ABSTRACT

Novel (hydrocarbylphenylsulfonyl)alkyltrimethyl stannanes and a process for preparing same are disclosed. These stannane compounds correspond to the following formula:

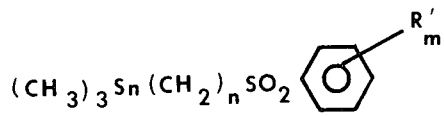

wherein R' is the same or different and is selected from the group consisting of linear and branched alkyl having 1 to 20 carbon atoms, cycloaliphatic having 4 to 6 carbon atoms and linear and branched alkenyl having 2 to 20 carbon atoms, $m$ is an integer from 1 to 3 and $n$ is an integer from 2 to 11.

The stannane compounds of this invention exhibit insecticidal properties when employed in insecticidal formulations.

7 Claims, No Drawings

(HYDROCARBYLPHENYLSULFONYL)ALKYL-TRIMETHYLSTANNANES

This application is a continuation-in-part of application Ser. No. 536,679, filed on Dec. 26, 1974 now abandoned.

RELATED CASE

The use of the compounds of this invention as insecticides is claimed in copending application of Strunk, Hubbard and Grahame, Ser. No. 640,983, filed concurrently herewith.

This invention relates to tetrasubstituted organotin compounds which are useful for controlling insects and pests. These tetrasubstituted organotins are new compounds.

BACKGROUND OF THE INVENTION

Organotin compounds are well known in the art and their application as biocides has likewise been well known for a long time in the art. The biocidal properties of a wide variety of organotin compounds, especially the tetra-substituted organotins, make them useful for the control of arachnid pests such as mites and ticks, fungi such as apple scab and woodrot organisms, weeds such as pigweed, and insects such as southern army worms, houseflies and Mexican bean beetles.

British Pat. No. 966,813 to Ziegler discloses a method for obtaining tetrasubstituted organotin compounds useful as high polymers, but no suggestion is made in this patent that these compounds might find utility in controlling insects and other pests.

U.S. Pat. No. 3,642,845 to Ramsden discloses bistrialkyltin compounds of the formula $(R)_3SnR'Sn(R)_3$ wherein R is an alkyl group and R' is a hydrocarbon diradical having a minimum of 8 carbon atoms. These compounds exhibit systemic pesticidal activity, particularly against lepidoptera insect larvae, such as the Southern army worm.

U.S. Pat. No. 3,206,489 to Stamm et al. discloses tetrasubstituted tin compounds of the general formula

wherein $R_1$, $R_2$, $R_3$ and $R_4$ can be alkyl radicals having from 1 to 12 carbon atoms and an aromatic hydrocarbon radical provided one of the R substituents is an alkyl radical terminating in a lower aliphatic thioacid group which is characterized by the presence of a thiocarboxyl function. These compounds are indicated as being useful as herbicides.

U.S. Pat. No. 3,591,614 to Bublitz discloses compounds of the formula

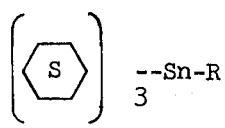

wherein R is 2-cyanoethyl, 2-carboxyethyl, or 2-carb-(lower)-alkoxyethyl group. These substituted ethyl derivatives of tricyclohexyltin as indicated as being useful as acaricides for the control of mites and ticks.

An additional U.S. Pat. No. 3,641,037 to Bublitz discloses compounds of the formula

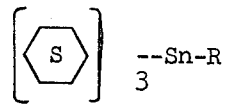

wherein R is 2-furyl, 2-pyridyl, 3-pyridyl, 1-indenyl, or 2-(2-pyridyl)ethyl, these compounds being useful as pesticides, particularly for the control of mites and ticks.

German patent 2,231,814 to Peterson discloses compounds of the formula $(R)_3SnCH_2-X$ wherein X is alkyl- or arylsulfonyl, alkyl- or arylthio or dialkylamino and R is alkyl of from 1 to 14 carbon atoms. These compounds are disclosed as being useful in protective coatings against bacteria, fungi, termites and barnacles.

Peterson, in U.S. Pat. No. 3,725,446, claims some of the same compounds, $R-S-CH_2-Sn-R'_3$, where R is alkyl of from 1 to 14 carbon atoms, aryl or substituted aryl, and R' is alkyl of 1 to 14 carbon atoms. These compounds are said to have pre-emergent and post-emergent herbicidal activity.

Peterson, in U.S. Pat. No. 3,784,580, discloses, inter alia, phenylsulfonylmethyltrihydrocarbyl stannane ((phenylsulfonylmethyl)trihydrocarbyltin) compounds of the formula $(R)_3SnCH_2SO_2Ph$, the said compounds being useful as insecticides, acaricides, bacteriostats, fungicides and herbicides. These Peterson compounds differ from the compounds of this invention in two important respects, namely, (1) the phenylsulfonyl moiety is linked to the tin atom by a single methylene diradical instead of by a diradical having at least two carbon atoms, and (2) the phenyl group lacks the hydrocarbyl substituents.

Peterson, in U.S. Pat. No. 3,794,670, discloses a process for the preparation of alkylphenylsulfonylmethyltrihydrocarbyl stannane ((alkylphenylsulfonylmethyl)trihydrocarbyltin) compounds of the formula $R_3SnCH_2SO_2R_1$, the said compounds being useful as pesticides and seed protecting agents. These Peterson compounds differ from the compounds of this invention in that the phenylsulfonyl moiety is linked to the tin atom by a single methylene diradical instead of by a diradical having at least two carbon atoms.

Peterson has authored a paper, "Preparation and Reactions of some Sulfur-Substituted Tetraorganotin Compounds", J. Organometal Chem. 26, 215–223 (1971). The following paragraph appears at page 218:

"[(Phenylsulfonyl)methyl]tributyltin [(IV)] was found to be unreactive toward carbon dioxide and oxygen at room temperature, while exposure of a thin layer of (IV) to air resulted in ca. 50% decomposition to phenyl methyl sulfone and tributyltin oxide within four days. These findings, when regarded in conjunction, are in accord with hydrolysis being responsible for the air sensitivity of (IV)."

Koopmans, in U.S. Pat. No. 3,031,483, discloses compounds of the structure

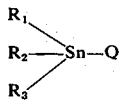

in which $R_1$, $R_2$ and $R_3$ may be the same or different and represent alkyl groups with 1–12 carbon atoms, phenyl groups or halophenyl groups, and Q represents one of a number of groups, including

These compounds have fungicidal and bactericidal properties.

Ayrey et al. have published a paper, J. Organometal. Chem. 35, 105–109 (1972), in which they deal with the preparation of 3-(trialkylstannyl)propyl aryl sulfides, $R_3SnCH_2CH_2CH_2SR'$. No utility is stated for these compounds.

THE INVENTION

The novel organotin compounds of this invention are tetrasubstituted tin compounds having the formula

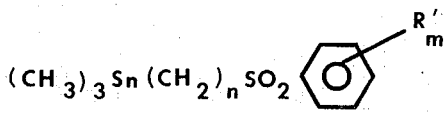

wherein R' is the same or different and is selected from the groups consisting of linear and branched alkyl having 1 to 20 carbon atoms, cycloaliphatic having 4 to 6 carbon atoms and straight chain and branched alkenyl having 2 to 20 carbon atoms, m is an integer from 1 to 3, and n is an integer from 2 to 11.

We recognize that the insecticidal and acaricidal activities of the compounds of the invention are derived from the trimethyltin segment of the molecule, i.e., $(CH_3)_3Sn-$. The degree and nature of activity of these compounds are also affected by the other moiety attached to the tin atom as, for example, oral and/or dermal mammalian toxicity, control of physical properties such as volatility and solubility, hydrolytic and/or oxidative stability, sensitivity to solar ultraviolet, ease of entry into the food chain, degradation by microorganisms and/or higher forms of life, and practical formulation and useful application rate.

In general, the compounds of the invention can be obtained according to the one-step reaction process described by R. Sommer and H. G. Kuivila, *J. Org. Chem.*, 33, 802 (1968), which involves reacting a compound containing an olefinic moiety with trimethyltin hydride, represented by the formula $(CH_3)_3SnH$, according to the following scheme:

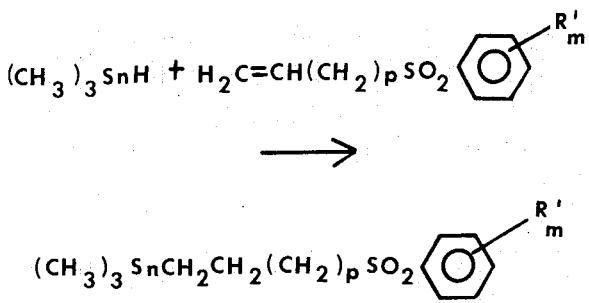

wherein R' and m are as defined above and p is an integer from 0 to 9.

In this synthesis, the substituted olefinic compounds and an equivalent amount of an organotin hydride are placed in a conventional glass reaction vessel under an inert atmosphere in the presence of a suitable solvent, where desired or as required, and with adequate stirring. The reaction mixture is irradiated under a mercury vapor lamp until no more organotin hydride is present, which is determined by infra-red spectrum analysis noting the absence of additional Sn-H absorption. The time for this to occur will vary depending upon the particular substituted olefinic compound used but will generally be about 4 to 48 hours, but, when n is 4 or higher, can be as long as 232 hours. The reaction mixture is normally maintained at a temperature of about 0° to 50° C. In cases where the reactants are heterogeneous and/or when the starting material is a solid, ether solvents such as diethyl ether and tetrahydrofuran, aromatic solvents such as benzene and toluene, esters and nitriles such as ethyl acetate and acetonitrile, alcohols such as methanol and ethanol, amides such as dimethylformamide, and the like, may be used to facilitate mixing of the reactants.

Where desired, purification of the organotin compounds can be achieved by using standard distillation, column chromatography, or recrystallization techniques.

Alternatively, the compounds of this invention can be made by the method of British Pat. No. 966,813 to Karl Ziegler using conventional free radical generators such as azobisisobutyronitrile, azotriphenylmethane and the like.

Examples of sulfones which can be used to prepare the compounds of this invention are listed below:

| | Compound No. |
|---|---|
| p-tolyl vinyl sulfone; | 2 |
| o-ethylphenyl vinyl sulfone; | |
| p-ethylphenyl vinyl sulfone; | 6 |
| p-n-propylphenyl vinyl sulfone; | |
| p-i-propylphenyl vinyl sulfone; | 7 |
| p-n-butylphenyl vinyl sulfone; | |
| p-s-butylphenyl vinyl sulfone; | |
| p-t-butylphenyl vinyl sulfone; | 1 |
| p-i-butylphenyl vinyl sulfone; | |
| p-n-amylphenyl vinyl sulfone; | 8 |
| p-n-hexylphenyl vinyl sulfone; | |
| p-n-heptylphenyl vinyl sulfone; | |
| p-n-octylphenyl vinyl sulfone; | 10 |
| p-t-octylphenyl vinyl sulfone; | |
| p-nonylphenyl vinyl sulfone; | |
| p-decylphenyl vinyl sulfone; | |
| p-dodecylphenyl vinyl sulfone; | 11 |
| p-tridecylphenyl vinyl sulfone; | 13 |
| p-cyclohexyl phenyl vinyl sulfone; | 19 |
| 3,4-dimethylphenyl vinyl sulfone; | |
| 2,4-dimethylphenyl vinyl sulfone; | 14 |
| 2,5-dimethylphenyl vinyl sulfone; | 15 |
| 2,4-diethylphenyl vinyl sulfone; | 16 |
| 2,5-diethylphenyl vinyl sulfone; | |
| 2,4-diisopropylphenyl vinyl sulfone; | |

-continued

| | |
|---|---|
| 2,5-diisopropylphenyl vinyl sulfone; | 17 |
| 2,5-di-t-butylphenyl vinyl sulfone; | |
| 2,5-dicyclohexylphenyl vinyl sulfone; | |
| 2,4,6-trimethylphenyl vinyl sulfone; | |
| 2,4,6-triethylphenyl vinyl sulfone; | |
| p-allylphenyl vinyl sulfone; | |
| p-propenylphenyl vinyl sulfone; | |
| p-crotylphenyl vinyl sulfone; | |
| p-methallylphenyl vinyl sulfone; | |
| p-4-pentenylphenyl vinyl sulfone; | |
| p-3-methylcrotylphenyl vinyl sulfone; | |
| p-oleylphenyl vinyl sulfone; | |
| 3-butenyl p-tolyl sulfone | |
| 3-butenyl p-t-butylphenyl sulfone; | 3 |
| 4-pentenyl p-ethylphenyl sulfone; | |
| 5-hexenyl p-tolylphenyl sulfone; | 4 |
| 6-heptenyl p-n-propylphenyl sulfone; | |
| 7-octenyl p-i-propylphenyl sulfone; | |
| 8-nonenyl p-n-butylphenyl sulfone; | |
| 9-decenyl p-s-butylphenyl sulfone; | |
| 10-undecenyl p-tolyl sulfone; | 5 |
| 4-pentenyl p-i-butylphenyl sulfone; | |
| 5-hexenyl p-n-amylphenyl sulfone; | |
| 6-heptenyl t-amylphenyl sulfone; | |
| 7-octenyl p-n-hexylphenyl sulfone; | |
| 8-nonenyl p-n-heptylphenyl sulfone; | |
| 9-decenyl p-octylphenyl sulfone; | |
| 10-undecenyl t-octylphenyl sulfone; | |
| 3-butenyl p-nonylphenyl sulfone; | |
| 4-pentenyl p-decylphenyl sulfone; | |
| 5-hexenyl p-n-dodecylphenyl sulfone; | |
| 6-heptenyl p-dodecylphenyl sulfone; | |
| 7-octenyl p-tridecylphenyl sulfone; | |
| 8-nonenyl p-cyclopentylphenyl sulfone; | |
| 9-decenyl p-cyclohexylphenyl sulfone; | |
| 3-butenyl 3,4-dimethylphenyl sulfone; | |
| 4-pentenyl 2,4-dimethylphenyl sulfone; | |
| 5-hexenyl 2,5-dimethylphenyl sulfone; | |
| 6-heptenyl 2,4-diethylphenyl sulfone; | |
| 7-octenyl 2,5-diethylphenyl sulfone; | |
| 8-nonenyl 2,4-diisopropylphenyl sulfone; | |
| 9-decenyl 2,5-diisopropylphenyl sulfone; | |
| 10-undecenyl 2,5-di-t-butylphenyl sulfone; | |
| 3-butenyl dicyclohexylphenyl sulfone; | |
| 4-pentenyl 2,4,6-trimethylphenyl sulfone; | |
| 5-hexenyl 2,4,6-triethylphenyl sulfone; | |
| 6-heptenyl 2,4,6-triisopropylphenyl sulfone; | |
| 7-octenyl 2,3,5,6-tetramethylphenyl sulfone; | |
| 8-nonenyl 2,3,4,5,6-pentamethylphenyl sulfone. | |

Trimethyltin hydride is prepared by known procedures such as are described in the following references:

K. Hayashi, J. Iyoda and I. Shiihara, J. *Organometal. Chem.*, 10, 81 (1967).

H. G. Kuivila, *Advan. Organometal Chem.*, 1, 47 (1964).

W. P. Neumann, *Angew. Chem., Internat. Edit.*, 2, 165 (1963).

Application of the compounds of the invention as insecticides can be carried out in a number of ways. For practical applications, the compounds of the invention can be used alone, or dissolved or suspended in suitable carriers such as water, alcohols, ketones, phenols, toluene or xylenes. Optionally, one or more surface active agents and/or inert diluents can be added to the formulation to facilitate handling. The formulations can take the form of dusts, granules, wettable powders, pastes, emulsifiable concentrates, aerosols, water solution concentrates, or a water soluble solid.

For example, the compounds of the invention can be applied as dusts when admixed with or absorbed on powdered solid carriers, such as the various mineral silicates, e.g., mica, talc, pyrophillite and clays, or as liquids or sprays when in a liquid carrier, as in solution in a suitable solvent such as acetone, benzene or kerosene, or dispersed in a suitable non-solvent medium, for example, water. The chemicals of the invention may be mixed with surface-active dispersing agents (see, e.g., U.S. Pat. No. 2,547,724, columns 3 and 4), with or without an organic solvent, as concentrates for subsequent addition of water to make aqueous suspensions of the chemicals of the desired concentration. The chemicals of the invention may be admixed with powdered solid carriers, such as mineral silicates together with a surface-active dispersing agent so that a wettable powder is obtained, or may be shaken with water to form a suspension of the chemical (and powdered solid carrier) in water for application in that form. The chemicals of the present invention may be applied by the aerosol method. Solutions for aerosol treatment may be prepared by dissolving the chemical directly in the aerosol carrier which is liquid under pressure but which is a gas at ordinary temperature (e.g., 20° C.) and atmospheric pressure, or the aerosol solution may be prepared by first dissolving the chemical in less volatile solvent and then admixing such solution with the highly volatile liquid aerosol carrier. The chemicals may be used admixed with carriers that are active themselves, for example, other insecticides or acaricides.

These formulations will contain amounts of the compounds effective for the particular method of control. These amounts can vary widely; typically, the range is from 0.1 to 95% active ingredient. Spray dilutions can contain from a few parts per million to full strength concentrates applied by ultra low volume techniques.

Commonly, the compounds are applied directly. To control aphids, for example, sprays of the compounds are applied to the aphids directly, to plants upon which they feed, or both. Sprays applied to the aphid-infested plants kill effectively even if direct contact does not occur, as where the aphids cling to the inner surface of a curled up leaf or lie in a protected leaf sheath of, for example, a grain plant. Another effective method of attack involves application of the compounds to the soil or other medium which insect-infested plants live. The compounds act systemically upon the insects after the compound is absorbed by the plants.

Harmful insects and related pests, such as mites, attack a wide variety of plants, including both ornamental and agricultural plants such as chrysanthemum, azalea, cotton, corn, wheat, apple and tobacco, and inflict damage by withdrawing vital juices from the plants, by secreting toxins and often by transmitting diseases. The compounds of the invention can prevent such damage. The methods of application, and the selection and concentration of these compounds will, of course, vary depending upon such circumstances as area, climate, prevalent diseases, etc. One skilled in the art can select the proper approach by simple experiments.

The following examples demonstrate the use of the above described procedures in obtaining the organotin compounds of this invention and their utilization as insecticides:

EXAMPLE 1

An 80 ml, two-necked, pyrex glass Schlenk reaction tube containing a Teflon coated magnetic stir bar was swept thoroughly with nitrogen and maintained in an air-free condition. The tube was charged with 9.5 g (42.5 mmoles) of 4-t-butylphenyl vinyl sulfone, 7.0 g (42.5 mmoles) of trimethyltin hydride and 10 ml. of toluene, stoppered, and placed in a 20°C water bath. The tube was irradiated for 35 hours by a 100 watt mercury vapor lamp which was situated in a large test tube and placed in the same bath 5–10 cm. from the reaction tube. Solvent was stripped off at reduced pressure on a rotary evaporator. Recrystallization of the solid product from cyclohexane gave 11.4 g of 2-(4-t-butylphenylsulfonyl)ethyltrimethylstannane, m.p. 118°–120°C. The presence of both the sulfonyl and trimethyltin groups was indicated by the strong infrared absorption bands at 1310 $cm^{-1}$, 1262 $cm^{-1}$, 1145 $cm^{-1}$ (—$SO_2$—) and 770 $cm^{-1}$ (($CH_3$)$_3$Sn) using a KBr disc. Nuclear magnetic resonance spectroscopy (NMR) showed the following:

The aromatic protons appeared as two multiplets each centered at 780 Hz and 754 Hz (each having 2 protons); the protons alpha to the sulfonyl moiety appeared as a complex multiplet centered at 312 Hz (2 protons); the methyl protons of the t-butyl group appeared as a singlet at 135 Hz (9 protons); the protons beta to the sulfonyl moiety appeared as a complex multiplet centered at 108 Hz (2 protons); the protons of the trimethyltin group appeared at 13 Hz, a singlet accompanied by a satellite band on either side (9 protons).

Analysis: Calc'd for $C_{15}H_{26}O_2SSn$ (percent): C, 46.30; H, 6.73; S, 8.24; Sn, 30.5. Found: C, 46.31; H, 6.68; S, 7.87; Sn, 28,62.

EXAMPLE 2

The procedure described in Example 1 was employed except that 7.74 g (42.5 mmoles) of 4-tolyl vinyl sulfone, 7.0 g (42.5 mmoles) of trimethyltin hydride and 10 ml of tetrahydrofuran were the reactants and solvent. The irradiation proceeded for 14.75 hours. Evaporation of solvent afforded an oil which crystallized on standing. Recrystallization of the product from cold petroleum ether gave 10.8 g of 2-(p-tolylsulfonyl)ethyltrimethylstannane, m.p. 55.5°–58°C. The presence of both the sulfonyl and trimethyltin groups was indicated by the strong infrared absorption bands at 1310 $cm^{-1}$, 1295 $cm^{-1}$, 1260 $cm^{-1}$, 1145 $cm^{-1}$ (—$SO_2$—) and 750 $cm^{-1}$ (($CH_3$)$_3$Sn) employing a KBr disc. Nuclear magnetic resonance spectroscopy (NMR) showed the following:

The aromatic protons appeared as two multiplets each centered at 773 and 730 Hz (2 protons each); the protons alpha to the sulfonyl moiety appeared as a complex multiplet centered at 309 Hz (2 protons); the methyl protons appeared as a singlet at 242 Hz (3 protons); the protons beta to the sulfonyl moiety appeared as a complex multiplet centered at 103 Hz (2 protons); the protons of the trimethyltin group appeared at 9.5 Hz, a singlet accompanied by one satellite band on either side (9 protons).

Analysis: Calc'd for $C_{12}H_{20}O_2SSn$ (percent): C, 41.53; H, 5.81; S, 9.24; Sn, 34.20. Found: C, 41.47; H, 5.80; S, 9.25; Sn, 34.43.

EXAMPLE 3

The procedure described in Example 1 was employed except that 10.7 g (42.5 mmoles) of 3-butenyl-4-t-butylphenyl sulfone and 7.0 g (42.5 mmoles) of trimethyltin hydride were the reactants. The irradiation proceeded for 70 hours. Recrystallization of the product from petroleum ether afforded 3.6 g of 4-(p-t-butylphenyl-sulfonyl)butyltrimethylstannane, m.p. 80°–81.8° C. The presence of both the sulfonyl and trimethyltin moieties was indicated by strong infrared absorption bands at 1300 $cm^{-1}$, 1282 $cm^{-1}$, 1147 $cm^{-1}$ (—$SO_2$—) and 780 $cm^{-1}$ [($CH_3$)$_3$Sn—] employing a KBR disc. Nuclear magnetic resonance spectroscopy (NMR) showed the following:

The aromatic protons appeared as two multiplets each centered at 777 and 753 Hz (each having 2 protons); the protons alpha to the sulfonyl moiety appeared as a complex multiplet centered at 307 Hz (2 protons); the methylene protons beta and gamma to the sulfone group appeared as a complex multiplet centered at 162 Hz (4 protons); the methyl protons of the t-butyl group appeared as a singlet at 134 Hz (9 protons); the methylene protons adjacent to the tin atom appeared as a complex moiety centered at 73 Hz (2 protons); the protons of the trimethyltin group appeared at the same chemical shift as tetramethylsilane (the internal standard)~1 Hz.

Analysis: Calc'd for $C_{17}H_{30}O_2SSn$ (percent): C, 48.94; H, 7.25; S, 7.68; Sn, 28.45. Found: C, 49.06; H, 7.33; S, 8.19; Sn, 27.60.

EXAMPLE 4

The procedure described in Example 1 was employed except that 10.1 g (42.5 mmole) of 5-hexenyl p-tolyl sulfone and 14.0 g (85 mmoles) of trimethyltin hydride were the reactants. The reaction mixture was irradiated for 232 hours. The excess trimethyltin hydride was allowed to evaporate from the reaction mixture under a flow of nitrogen. The unreacted 5-hexenyl p-tolyl sulfone was removed from the reaction mixture by distillation at I × $10^{-3}$ mm Hg leaving 3.25 g of crude product. Column chromatography of the distillation residue over silica gel, employing toluene and 1% acetone in toluene as eluents, afforded an oil, 6-(p-tolylsulfonyl)-hexyltrimethylstannane. The presence of both the sulfonyl and trimethyltin moieties was indicated by the strong infrared absorption bands at 1315 $cm^{-1}$, 1300 $cm^{-1}$, 1285 $cm^{-1}$ and 1140 $cm^{-1}$ (—$SO_2$—) and 760 $cm^{-1}$ [($CH_3$)$_3$Sn-]. NMR showed the following:

The aromatic protons appeared as two multiplets each centered at 775 and 732 Hz (2 protons each); the protons alpha to the sulfonyl group appeared as a complex multiplet centered at 303 Hz (2 protons); the methyl protons of the tolyl group appeared as a singlet at 243 Hz (3 protons); the methylene protons beta through epsilon to the sulfone group appeared as a broadened complex multiplet centered at 147 Hz (8 protons); the protons of the methylene group attached to the tin atom appeared as a triplet centered at 74 Hz (2 protons); the protons of the trimethyltin group appeared as a singlet at —2 Hz accompanied by one satellite band on either side (9 protons).

Analysis: Calc'd for $C_{16}H_{28}O_2SSn$ (percent): C, 47.67; H, 7.00. Found: C, 47,52; H, 7.07.

EXAMPLE 5

The procedure described in Example 1 was employed except that 13.1 g (42.5 mmoles) of 10-undecenyl-p-tolyl sulfone and 14.0 g (85 mmoles) of trimethyltin hydride were the reactants. The reaction mixture was irradiated for 189 hours. The excess trimethyltin hydride was allowed to evaporate from the reaction mixture under a flow of nitrogen. The residual oil weighed 15.5 g. One-half of the crude product was chromatographed on a column containing silica gel using toluene and 2% acetone in toluene as eluents. The product, 11-(p-tolylsulfonyl)-undecyltrimethylstannane, was obtained as an oil. The presence of both the sulfonyl and trimethyltin groups was indicated by the strong infrared absorption bands at 1315 $cm^{-1}$, 1300 $cm^{-1}$, 1285 $cm^{-1}$, 1140 $cm^{-1}$ (—$SO_2$) and 760 $cm^{-1}$ [($CH_3$)$_3$Sn—]. NMR showed the following:

The aromatic protons appeared as two multiplets each centered at 771 and 728 Hz (2 protons each); the protons alpha to the sulfonyl moiety consisted of a multiplet centered at 300 Hz (2 protons); the methyl protons of the tolyl group appeared as a singlet at 240 Hz (3 protons); the methylene [—(CH$_2$)$_9$—] appeared as a broadened multiplet with peak maxima at 161 and 119 Hz (18 protons); the methylene protons alpha to the tin atom appeared as a triplet centered at 76 Hz (2 protons); the protons of the trimethyltin group appeared as a singlet at 0 Hz accompanied by one satellite band on either side (9 protons).

Analysis: Calc'd for $C_{21}H_{38}O_2SSn$ (percent): C, 53.29; H, 8.09. Found: C, 53.81; H, 8.09.

EXAMPLE 6

Using the procedures and apparatus described above and detailed in Example 1, additional organotin compounds of this invention were prepared and, along with the products of Examples 1–5, are identified in Table I below wherein the expression "high vacuum" denotes a pressure of at least 0.1 mm Hg. Table I also indicates those instances where a solvent was used and/or the compound was purified as well as the melting point. All of the compounds are identified as stannanes since they can be regarded as substitution products of "stannane", i.e., SnH$_4$.

Compound 20, and similar compounds in which $n = 3$ or more, can be prepared by an alternative method from those shown above, the starting materials being:

a. $(CH_3)_3Sn(CH_2)_n\text{-}Z$, where Z is chlorine, bromine or iodine; and b. AlkSO$_2$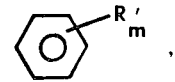

where Alk is sodium, potassium or lithium.

Suitable type (a) starting materials include:

4-bromobutyltrimethylstannane;
3-chloropropyltrimethylstannane;
5-bromopentyltrimethylstannane;
6-chlorohexyltrimethylstannane;
7-bromoheptyltrimethylstannane;
8-iodooctyltrimethylstannane;
9-chlorononyltrimethylstannane;
10-bromodecyltrimethylstannane;
11-bromoundecyltrimethylstannane.

Suitable type (b) starting materials include:

Table I

Organotin Compounds of the Formula $(CH_3)_3Sn(CH_2)_nSO_2\text{-}C_6H_{(4-m)}R'_m$

| Compound No. | Stannane Compound | R' | m | n | Reaction Solvent | Purification Method | m.p.,°C. |
|---|---|---|---|---|---|---|---|
| 1 | 2-(p-t-butylphenylsulfonyl)ethyltrimethyl | t-butyl | 1 | 2 | toluene | recrystall'n | 118–20 |
| 2 | 2-(p-tolylsulfonyl)ethyltrimethyl | methyl | 1 | 2 | tetrahydrofuran | recrystall'n | 55.5–58 |
| 3 | 4-(p-t-butylphenylsulfonyl)butyltrimethyl | t-butyl | 1 | 4 | none | recrystall'n | 80–81.8 |
| 4 | 6-(p-tolylsulfonyl)hexyltrimethyl | methyl | 1 | 6 | none | column chromatography | oil |
| 5 | 11-(p-tolylsulfonyl)undecyltrimethyl | methyl | 1 | 11 | none | column chromatography | oil |
| 6 | 2-(p-ethylphenylsulfonyl)ethyltrimethyl | ethyl | 1 | 2 | tetrahydrofuran | recrystall'n | 52–56.5 |
| 7 | 2-(p-isopropylphenylsulfonyl)ethyltrimethyl | isopropyl | 1 | 2 | tetrahydrofuran | recrystall'n | 53–57.5 |
| 8 | 2-(p-n-pentylphenylsulfonyl)ethyltrimethyl | n-pentyl | 1 | 2 | toluene | high vacuum | oil |
| 9 | 2-[p-(1,1-dimethylpropyl)phenylsulfonyl]ethyltrimethyl | 1,1-dimethylpropyl | 1 | 2 | toluene | recrystall'n | 72–74 |
| 10 | 2-(p-octylphenylsulfonyl)ethyltrimethyl | n-octyl | 1 | 2 | tetrahydrofuran | high vacuum | oil |
| 11 | 2-(p-dodecylphenylsulfonyl)ethyltrimethyl | dodecyl (branched) | 1 | 2 | tetrahydrofuran | high vacuum | oil |
| 12 | 2-(p-n-dodecylphenylsulfonyl)ethyltrimethyl | n-dodecyl | 1 | 2 | toluene | recrystall'n | 33–34 |
| 13 | 2-(p-n-tridecylphenylsulfonyl)ethyltrimethyl | n-tridecyl | 1 | 2 | toluene | recrystall'n | 43.3–4408 |
| 14 | 2-(2,4-dimethylphenylsulfonyl)ethyltrimethyl | methyl | 2 | 2 | tetrahydrofuran | high vacuum | oil |
| 15 | 2-(2,5-dimethylphenylsulfonyl)ethyltrimethyl | methyl | 2 | 2 | tetrahydrofuran | high vacuum | oil |
| 16 | 2-(2,4-diethylphenylsulfonyl)ethyltrimethyl | ethyl | 2 | 2 | tetrahydrofuran | high vacuum | oil |
| 17 | 2-(2,5-diisopropylphenylsulfonyl)ethyltrimethyl | isopropyl | 2 | 2 | tetrahydrofuran | high vacuum | oil |
| 18 | 2-(p-cyclopentylphenylsulfonyl)ethyltrimethyl | cyclopentyl | 1 | 2 | tetrahydrofuran | recrystall'n | 94–95 |
| 19 | 2-(p-cyclohexylphenylsulfonyl)ethyltrimethyl | cyclohexyl | 1 | 2 | tetrahydrofuran | recrystall'n | 116–118 | sodium p-toluenesulfinate;
sodium p-ethylbenzenesulfinate;
sodium p-n-propylbenzenesulfinate;
sodium p-i-propylbenzenesulfinate;
sodium p-n-butylbenzenesulfinate;
sodium p-s-butylbenzenesulfinate;
sodium p-t-butylbenzenesulfinate;
sodium p-i-butylbenzenesulfinate;
sodium p-n-amylbenzenesulfinate;
sodium p-t-amylbenzenesulfinate;
sodium p-n-hexylbenzenesulfinate;
sodium p-n-octylbenzenesulfinate;
sodium p-n-nonylbenzenesulfinate;
sodium p-n-decylbenzenesulfinate;
sodium p-n-undecylbenzenesulfinate;
sodium p-n-dodecylbenzenesulfinate;
sodium p-n-tridecylbenzenesulfinate;
sodium p-cyclohexylbenzenesulfinate;
sodium 2,4-dimethylbenzenesulfinate;
sodium 2,5-dimethylbenzenesulfinate;
sodium 2,4-diethylbenzenesulfinate;
potassium 2,5-diisopropylbenzenesulfinate;
potassium 2,4,6-trimethylbenzenesulfinate.

The specific preparative details for Compound 20 are presented below. The reaction times range from 0.5 to 24 hours and suitable reaction temperatures are from 20° to 120° C. The catalyst can be any phase transfer catalyst as shown by E.V. Dehmlow, Chem. Tech. (1975), starting at page 210, which citation is hereby incorporated by reference.

EXAMPLE 7

Into a 125 ml single-necked round bottom flask fitted with a teflon coated magnetic stir bar and a reflux condenser was charged 4.45 g of sodium p-toluenesulfinate, 20 ml water, 10 ml toluene, 7 g of 75% 4-bromobutyltrimethylstannane and 0.44 g of tri-n-butyl-hexadecylphosphonium bromide. The mixture was refluxed for 2.5 hours with rapid stirring. On cooling, the organic phase was separated, dried over anhydrous magesium sulfate and stripped of solvent on a rotary evaporator. The oil residue was distilled two times through a short path distillation head. The second distillation afforded 3.3 g of 4-(p-tolylsulfonyl)butyltrimethylstannane, b.p. 136°–140° C. (1 × $10^{-3}$ mm Hg). The presence of both the sulfonyl and trimethyltin moieties was indicated by strong infrared absorption bands at 1315 $cm^{-1}$, 1300 $cm^{-1}$, 1142 $cm^{-1}$ ($—SO_2—$) and 765 $cm^{-1}$ [$(CH_3)_3Sn—$]. NMR spectroscopy showed the following:

The aromatic protons appeared as two multiplets each centered at 768 Hz and 726 Hz (each having 2 protons); the protons alpha to the sulfonyl group appeared as a complex multiplet centered at 291 Hz (2 protons); the beta and gamma methylene protons appeared as a complex multiplet centered at 157 Hz (4 protons); the p-tolyl methyl group appeared as a singlet at 244 Hz (3 protons); the methylene proton adjacent to the tin atom appeared as a complex multiplet centered at 74 Hz (2 protons); the protons of the trimethyltin group appeared as a singlet, flanked on either side by satellite bands, at −4 Hz from the tetramethylsilane internal standard (9 protons).

Analysis: Calc'd for $C_{14}H_{24}O_2SSn$ (percent): C, 44.83; H, 6.45; S, 8.55; Sn, 31.64. Found: C, 44.98; H, 6.61; S, 8.46; Sn, 31.65.

EXAMPLE 8

The organotin compounds of this invention were tested as insecticides according to the following procedures:

A. Mosquito Larvae Test

Formulations were prepared by dissolving 30 mg of organotin compound of the invention in 10 ml of acetone. This solution was then diluted to 1 ppm with water. Two 25-ml aliquots were placed in test tubes to which were added 10 to 25 fourth instar larvae of the yellow fever mosquito, Aedes aegypti (Linnaeus). The tubes were held in darkness for 72 hours. At the end of this period the percent control was determined.

B. Aphid Contact Test

Test formulations were prepared for spraying at 1000 ppm (parts per million) concentration by dissolving them in a small amount of acetone and adding a suitable wetting agent. Typically, 0.6 gram of organotin compound was dissolved (or suspended) in 10 ml of acetone, 2 drops of Triton-X100 wetting agent (octylphenoxy polyethoxy ethanol with 9-10 mole percent of polyethylene oxide) were added and this was suspended in 300 ml of water make a 6000 ppm suspension. An aliquot was then further diluted with distilled water to 1000 ppm concentration of organotin compound.

Eight to ten day old barley seedlings, grown ten plants each in a 12 oz. cup, were infested with corn leaf aphids Rhopalosiphum maidis (Fitch), two days prior to treatment. Two pots were treated with each formulation by spraying with a spray atomizer while the plants were rotating on a turntable. Following treatment, the plants were held for 5 days in the greenhouse. At the end of this period, the percent control of the aphids was estimated based on the reduction of the population density as compared to untreated plants used as controls.

C. Tobacco Bud Worm Diet Test

Test formulations were prepared at 1000 ppm as in B, the Aphid Contact Test, above. Two-tenths ml of the diluted formulations was pipetted onto the surface of 5 grams of a synthetic diet mixture held in partially filled cells of a plastic jelly tray. Five cells were treated with each chemical dilution. The diet mixture was a modified Vanderzant diet consisting of wheat germ, soy flour, agar, sugar, salts, vitamins, preservatives and water. The jelly trays had fifty cavities per sheet, each cavity being approximately 2.5 × 4.0 × 1.5 cm.

Following treatment, a third or early fourth instar larva of the tobacco bud worm, Heliothis virescens (Fabricius), was placed in each cell. The trays were then covered with a plastic film plus a sheet of rigid plastic and were held in an incubator at 80° F.

At the end of one week, the trays were examined and the percent control was determined, adjusted for any natural mortality in the controls by Abbott's formula. The trays were held an additional week and any abnormalities in the development of the survivors was noted.

D. Cotton Boll Weevil Test

Formulations were prepared at 1000 ppm as in B, the Aphid Contact Test, above. Cotton seedlings 12 to 14 days old grown in 12 oz cups were used. Two pots were treated with each formulation by spraying with a spray atomizer while rotating the pots on a turntable. Five adult cotton boll weevils, Anthonomous grandis Boheman, were placed in each pot following treatment and were caged by covering the pots with an inverted 16 oz styrofoam cup with small perforations punched in the bottom. The surviving weevils were counted after five days in the greenhouse to determine the percent control, corrected for any natural mortality in the control plants by Abbott's formula. The percent reduction in feeding was estimated by visual comparison of the feeding damage to the treated plants with the control (untreated) plants.

E. Mite One-Day Residual Test

Test compounds were prepared as in B, the Aphid Contact Test, above but were further diluted to 500 ppm with water.

Cotton, in the second primary leaf stage grown in twelve ounce cups under greenhouse conditions at 70°–75° F., was used in the test.

one plant (two primary leaves) in one pot was used for each replicate; two replicates were used for each concentration of organotin compound tested.

The plants were sprayed with the dispersions using a small spray atomizer to throughly drench the foliage.

One day following treatment, a circle of tree tanglefoot was placed on the upper surface of the treated leaves and adult mites, *urticae* Koch, were transferred into this confinement.

Six days following infestation with mites, the plants were examined for adult live mites remaining on the leaves. On an estimation basis in comparison with the number of living mites on the control plants, the percent control was determined.

F. Abbott's Formula:

$$\text{Adjusted \% mortality} = \frac{\text{\% alive in check} - \text{\% alive in treated}}{\text{\% alive in check}} \times 100$$

The results of the above-described tests are set forth in Table II below.

Table II

| Compound No. | Organotin Compounds as Insecticides | | | | | |
|---|---|---|---|---|---|---|
| | % Control Mosquito Larvae 1 PPM | % Control Aphids 1000 PPM | % Control Tobacco Bud Worm 1000 PPM | % Control Cotton Boll Weevil 1000 PPM | Boll Weevil % Feeding Reduced on Cotton | Mite One-Day Residual 500 PPM |
| 1 | 100 | 100 | 100 | 100 | 95 | 100 |
| 2 | 100 | 100 | 100 | 100 | — | 100 |
| 3 | 100 | 95 | 100 | 87 | 95 | 100 |
| 4 | 100 | 100 | 100 | 100 | 100 | 100 |
| 5 | 100 | 80 | 60 | 100 | 100 | 100 |
| 6 | 100 | 100 | 100 | 88 | 100 | 100 |
| 7 | 100 | 100 | 100 | 88 | 100 | 100 |
| 8 | 100 | 100 | 100 | 78 | 95 | 100 |
| 9 | 100 | 100 | 100 | 100 | 100 | 100 |
| 10 | 100 | 100 | 100 | 90 | 50 | 100 |
| 11 | 100 | 90 | 100 | 100 | 50 | 100 |
| 12 | 100 | 90 | 100 | 100 | 95 | 100 |
| 13 | 100 | 0 | 100 | 100 | 100 | 100 |
| 14 | 100 | 95 | 100 | 80 | 100 | 100 |
| 15 | 100 | 100 | 100 | 100 | 90 | 100 |
| 16 | 100 | 100 | 100 | 100 | 100 | 100 |
| 17 | 100 | 100 | 100 | 100 | 100 | 100 |
| 18 | 100 | 20 | 100 | 100 | 100 | 100 |
| 19 | 100 | 93 | 100 | 90 | 95 | 100 |
| 20 | 100 | 100 | 100 | 90 | 100 | 100 |

| Comparative Data | % Control Mosquito Larvae 1 PPM | % Control Aphids 1000 PPM | % Control Tobacco Bud Worm 1000 PPM | % Control Cotton Boll Weevil 1000 PPM | Boll Weevil % Feeding Reduced on Cotton | Mite One-Day Residual 500 PPM |
|---|---|---|---|---|---|---|
| Stamm et al. 3,206,489 $(nC_4H_9)_3SnCH_2CH_2-S-\overset{O}{\overset{\|}{C}}CH_3$ 2-Thioacetoxyethyltri-n-butyltin | 55 | 95 | 20 | 40 | 90 | 80 |
| Koopmans et al. 3,031,483 $(CH_3)_3SnO\overset{O}{\overset{\|}{S}}$—⟨O⟩—$CH_3$ Trimethyltin p-toluenesulfinate | 0 | 98 | 100 | 100 | 100 | 100 |

The Stamm et al. compound, for which data are presented at the end of Table II, was prepared in accordance with Example 1 of the Stamm et al. patent. The Koopmans et al. compound, for which data are similarly presented, was prepared as follows.

In a 250 ml Erlenmeyer flask was placed a solution of 5.95 g. (0.033 mole) of

in 50 ml. H$_2$O. Then 6.6 g. (0.033 mole) (CH$_3$)$_3$SnCl in 100 ml. acetone was added dropwise. A white precipitate formed. The reaction mixture was heated to 60° C. for 20 minutes. After stirring overnight, the acetone was removed by evaporation and a white viscous residue separated. The water layer was decanted. The viscous residue was treated with 50 ml. of petroleum ether. A solidified product (8.1 g.), having a m.p. of 98°–102° C., was isolated. Peter M. Slegen, Univ. of North Carolina, Ph.D. thesis 1967, reported m.p. 97°–101° C. for trimethyltin p-toluenesulfinate. The I.R. exhibited strong absorption at 955 cm$^{-1}$ and 990 cm$^{-1}$.

As can be seen from the results set forth in Table II above, the organotin compounds of the invention exhibit good to superior insecticidal activity for a wide variety of insects, especially in comparison with the two prior art compounds.

EXAMPLE 9

MITE ONE-DAY RESIDUAL TEST OF ORGANOTIN COMPOUNDS AT DIFFERENT FORMULATION CONCENTRATIONS

In this example, test formulations were prepared to contain different concentrations of organotin compounds of the invention. The method employed was as follows:

Cotton in the second primary leaf stage, grown in twelve ounce cups under greenhouse conditions at 70°–75° F. was used in this test. One plant (two primary leaves) in one pot was used for each replicate and two replicates were used for each concentration of tin compound tested. Test formulations were prepared by dissolving 50 mg of tin compound in one ml of acetone, adding one drop of Emulfor 719, a commercial surface-active dispersing agent (polyoxyethylated vegetable oil) and suspended in 50 ml of water for concentration of 1000 ppm (parts per million). Aliquots of this solution were further diluted with distilled water to concentrations of 100, 20 and 5 ppm. The plants were sprayed with the formulations using a small spray atomizer to thoroughly drench the foliage. One day following treatment, a circle of tree tanglefoot was placed on the upper surfaces of the treated leaves and adult mites, *Tetranychus urticae* koch, were transferred into this confinement. Counts of these mites were made immediately following transfer and again six days later.

Abbott's formula was used to compensate for check mortality and to obtain the adjusted percent control. The results are shown in Table III below:

Table III

| Compound No. | Mite One-Day Residual Test % Control | | |
|---|---|---|---|
| | 100 PPM | 20 PPM | 5 PPM |
| 1 | 100 | 68 | 49 |
| 2 | 100 | 79 | 4 |
| 6 | 100 | 93 | 0 |
| 7 | 100 | 100 | 30 |
| 14 | 100 | 95 | 2 |
| 19 | 78 | 6 | 40 |

The results above clearly indicate that the selected organotin compounds of the invention exhibit a high degree of effectiveness at different levels of concentration.

EXAMPLE 10

TOBACCO BUD WORM - COTTON TEST

The test formulations in this example were also prepared to contain different concentrations of compounds of the invention which were then tested according to the procedure described below:

Tesst formulations were prepared by dissolving 50 mg of organotin compound of the invention in one ml of acetone, adding one drop of Emulfor 719, a commercial surface-active dispersing agent (polyoxyethylated vegetable oil) and suspending in 50 ml of water for a concentration of 1000 ppm (parts per million). Aliquots of the solution were further diluted with distilled water to concentrations of 100, 20 and 5 ppm.

Cotton seedlings two weeks old were used. These were grown in 12 ounce cups with two plants in each cup. The diluted formulations were applied to the seedling plants with a spray atomizer and allowed to dry. Three cups were treated with each diluted formulation. A third instar larvae of the tobacco bud worm, *Heliothis virescens* (Fabricius), was placed in each cup and confined by inverting a perforated 16 oz. styrofoam cup over the top. Percent control of the worms and amount of feeding damage to the plants was determined after two weeks in the greenhouse.

The results of this test are set forth in Table IV below:

Table IV

| | Tobacco Bud Worm on Greenhouse Cotton % Control | | |
|---|---|---|---|
| Compound of | 100PPM | 20 PPM | 5 PPM |
| Example 1 | 100 | 100 | 50 |

As can be seen from the results shown in Table IV above, the organotin compound of the invention is generally excellent in controlling this type of insect.

EXAMPLE 11

APHID - SOIL DRENCH TEST

This example is similar to Examples 9 and 10 above in that test formulations containing different concentrations of organotin compounds were prepared and then tested according to the following procedure:

Test formulations were prepared by dissolving 10 mg of organotin compound of the invention in one ml of acetone plus one drop (about 30 mg) of Emulfor 719, the same surface-active agent identified in Example 9 above, and diluting with water to 100 ml for a concentration of 100 ppm of the test organotin compound in water. Further dilutions were made to 10 ppm and 1 ppm with water.

Barley seedlings eight days old, grown in 12 ozccups, 10 plants per cup, with a total weight, including the soil, of approximately 440 grams, were used. The seedlings were deliberately infested with corn leaf aphids, *Rhopalosiphum maidis* (Fitch), a day prior to treatment. Twenty-two ml aliquots of the dilute formulations were drenched on the surface of the cups, but not over the infested plant parts. Two cups were treated with each rate. Rates were calculated in pounds per acre based on a weight of 440 gms/cup and assuming an acre of soil seven inches deep weighs two million pounds.

The percent control was determined by observations made one week following treatment. The results are set forth in Table V below wherein "No./A" denotes the calculated pounds per acre.

Table V

| | Barley Soil Drench % Control of Aphids | | |
|---|---|---|---|
| Compound of | 10 lbs./A | 1 lbs./A | 0.1 lbs./A |
| Example 1 | 86 | 30 | 0 |

This test demonstrates that the chemical of this invention is also effective as a systemic insecticide on barley plants in that they absorb sufficient amounts of the organotin compound of the invention to effectively control aphids.

As is brought out above in the discussion of prior art under "Background of the Invention", a Peterson sulfonyl compound was reported as being subject to hydrolysis on being exposed to air. The work reported in the following Example serves as confirmation of this conclusion.

EXAMPLE 12

A. The compound subjected to humid air was a typical Peterson compound, phenylsulfonylmethyltrimethylstannane,

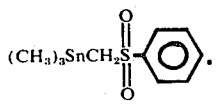

A 5 gal. jar was set on its side on a wooden support and contained a wire mesh screen to support samples in test over a mixture of 152 g of $(NH_4)_2SO_4$ in 168 g of $H_2O$. An excess of $(NH_4)_2SO_4$ in contact with a saturated aqueous solution of $(NH_4)_2SO_4$ gives 81% humidity in a closed space.[1] The following samples of this Peterson compound were weighted into 40 mm O.D. petri dishes (minus cover) of 8 mm depth and the dishes placed into the humidity chamber, and the chamber was then closed: No. 15 dish 0.2186 g; No. 34 dish 0.2006 g. Before the samples were removed from the balance, a solid crust began forming on the surface of the liquid and, inside of ten minutes, covered all of the liquid surface. An odor of a volatile trimethyltin compound was noted. When the samples were placed in the humidity chamber, the samples coated almost all of the surface area inside the dishes. The 5 gal. jar was set on the bench under normal laboratory lighting. The initial temperature inside the chamber was 24.5° C. Over 4 days, the temperature ranged from the initial temperature as a high to a low temperature of 18° C. The No. 15 sample was removed after 4 days. Under the surface crust, there was an oily solid. The sample was scraped with a spatula into a 2 dram sample vial. The oily solid remaining was washed into the vial with chloroform (about 0.5 to 1 ml). The chloroform was removed under a stream of nitrogen. The No. 34 sample was removed from the chamber after 7 days. The sample was completely solid and was scraped into a vial. The NMR spectra for both samples showed that, in addition to the aromatic absorptions, there was one singlet due to $CH_3$ of the hydrolysis product,

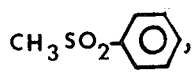

at 307 Hz and a broadened singlet flanked by satellites at 36.5 Hz for $(CH_3)_3Sn$ and a broadened singlet at 191 Hz for the OH. These results indicate the formation of a mixture of trimethyltin hydroxide and methylphenyl sulfone. There was no unreacted starting Peterson compound.

[1] Handbook of Chemistry and Physics, Chem. Rubber Pub. Co., p. 2500 (1960).

B. A corresponding compound, closely related to the compounds of this invention, phenylsulfonylethyltrimethylstannane,

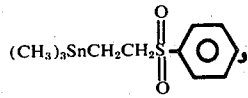

was subjected to similar humidity conditions in the same equipment. The following samples of the indicated compound, purified by column chromatography, were weighed into small petri dish covers and placed in the 81% humidity chamber at a temperature of 27° C.: Dish No. 15 0.2426 g; Dish No. 34 0.2020 g. Over the period of the test, the temperature was maintained at room temperature. The No. 34 sample was removed from the chamber after 4 days and an infrared spectrum was run within several minutes. This showed no additional absorption bands from those of the starting material. The No. 15 sample was removed from the chamber after 2 weeks. The infrared spectrum of this sample was superimposable with the spectrum of the starting material. No additional absorption bands were present. The NMR spectra for both samples were identical to that for the starting material. It is thus established that the tested compound of this invention is not subject to hydrolysis under the stated conditions.

*See page 48, lines 5–8.

The following represents an attempt to follow the general procedure of U.S. Pat. No. 3,794,670 of Peterson for the preparation of a compound of this invention, 2-[p-t-butylphenylsulfonyl]ethyltrimethylstannane,

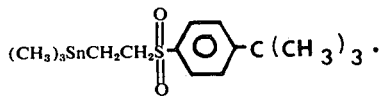

However, the compound obtained is shown to be 1-[p-t-butylphenylsulfonyl]ethyltrimethylstannane,

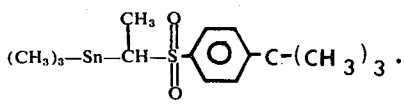

This suffers from the same hydrolysis deficiencies as does the Peterson compound of the preceding Example.

EXAMPLE 13

The equipment utilized was a 500 ml 3-necked round bottom flask fitted with mechanical stirrer, $N_2$ inlet with Y-tube, 125 ml addition funnel (flame dried and $N_2$ filled) and ice water bath; for later use: simple distillation take-off, thermometer and oil bath. The materials used were:

1. 140.0 ml (total volume) reagent benzene distilled to remove water azeotrope.
2. 18.5 ml (13.1 g, 0.18 mole) diethylamine (dried).
3. 94.0 ml (0.15 mole) 1.6 molar n-butyllithium in n-hexane.
4. 29.8 gm (0.15 mole) trimethyltin chloride.

5. 33.9 gm (0.15 mole) p-t-butylphenylethylsulfone (mol. wt. 226.3).

All syringes used were previously oven dried at 110° C. and cooled under $N_2$. The diethylamine (via syringe) + 50 ml of benzene (via syringe) were introduced into the flask. The butyllithium was placed into the addition funnel (via springe). The reaction flask was cooled with mechanical stirring using the ice water bath and the butyllithium was added dropwise over a period of 33 minutes. The reaction solution was now milky white. The addition funnel was rinsed with 10 ml of benzene (via syringe) and drained directly into the reaction flask. Into a $N_2$ flushed 125 ml Erlenmeyer flask the trimethyltin chloride was weighed out and dissolved in 50 ml of benzene (via springe) and poured into the addition funnel (via syringe). An additional 25 ml benzene was used to rinse the flask, and was then added to the addition funnel. While keeping the reaction mixture at 0°–5° C. with the ice bath, the tin chloride solution was added dropwise over a period of 1 hour. The reaction mixture was then allowed to warm to room temperature with stirring for 1 hour and 10 minutes. The sulfone was weighed out and added directly as a solid, and readily dissolved. The mixture was stirred for ½ hour at room temperature and kept overnight under $N_2$. The reaction mixture was a milky light tan.

In the morning, the apparatus was adapted for thermometer, – using an immersion thermometer, reflux thermomoeter, oil bath thermometer plus joint and condenser and a 300 ml flat bottom 1-neck receiver flask — all under nitrogen.

was vacuum filtered using a 15 cm Buchner filter, —keeping covered and avoiding air suction through the funnel to avoid moisture contact. The slightly turbid filtrate was treated with Darco G 60 at room temperature for about 1.5 hours and gravity filtered (kept covered) into a tared 1 liter, 1-neck round bottom flask, and the $CHCl_3$ was stripped on a Rotovac (Rotovac vented under $N_2$) leaving a clear brown, slightly viscous liquid having crude yield of 46.2 gms.

TLC (thin layer chromatography) on silica gel (Eastman) (9/1 volume ratio cyclohexane/EtoAc) showed two large spots with distances from the origin of 25 mm and 37 mm. The shorter distance spot had the same distance as that for the starting ethylsulfone. The spots were approximately of equal size and intensity when observed under short wave U.V. The oil was subjected to vacuum distillation through a short path head using a single 50 ml receiver. An oil was collected between 120°–154° C. at 0.06–0.12 mm Hg. The pot temperature ranged between 150° and 200° C. There appeared to be no separation points using this short path. The oil distillate formed some solid which was isolated by decantation of the oil and pressing the solid on filter paper: 3.86 g. The solid was recrystallized from petroleum ether, m.p. 43°–65°. TLC of this material showed 2 spots the same as the crude product. The distillate oil was redistilled through a microware, vacuum jacketed Vigreaux column. Cut No. 1: b.p. 48°–112.5° (2.5–3 $\times 10^{-3}$ mm). TLC showed a large spot (starting sulfone) and a faint spot for product. Cut No. 2: b.p. 108°–136° (2-8 $\times 10^{⅓3}$ mm). TLC showed a large spot for starting Table VI

| Elapsed Time | Oil Bath Temperature | Internal Pot Temperature | Reflux Temperature | |
|---|---|---|---|---|
| Start | 54 | 37.5 | 24 | (R.T.) |
| 15 mins. | 69 | 55.0 | 24 | |
| 22 mins. | 84 | 64 | 49 ↑ | (Distillate coming over into receiver) |
| 25 mins. | 86 | 66 | 54 | |
| 35 mins. | 83 | 73.5 | 61.5 | |
| 46 mins. | 95.5 | 77 | 70 | (Schlieren effect present in receiver) |
| 1 hr. 5 mins. | 100 | 83 | 72 | (Schlieren effect present in receiver) |
| 1 hr. 45 mins. | 110 | 95 | 73 | |
| 2 hrs. | 117 | 105 | 75.5 | |
| 2 hrs. 15 mins. | 123.5 | 112 | 70 | (Take-off decreasing) |
| 3 hrs. 20 mins. | 125 | 115 | 50.5 | (Ceased. Pot contents cloudy; brown slurry) |
| 3 hrs. 55 mins. | 125 | 115 | 60 | (Stirring slowed; some drops over) |
| 4 hrs. 5 mins. | 125.5 | 115.5 | 49 | (Occasional drops) |
| 4 hrs. 15 mins. | 124.5 | 115.5 | 44 | |
| 4 hrs. 50 mins. | 123 | 113 | 43 | (Start $N_2$ sweep through reaction flask to receiver and refluxed back to 66°. Pot temp. to 111° and distillate coming over.) |
| 5 hrs. 5 mins. | 123 | 113 | 57.5 | (Occasional drops) |
| 5 hrs. 15 mins. | 123.5 | 114 | 51 | (Occasional drops; let cool to R.T. under $N_2$.) |

The distillation apparatus was disassembled when cool. The receiver was kept under $N_2$ with stirring, and cooled down to 0°–5° C. with ice bath. A thick, light brown slurry resulted. 4.0 gms (3.4 cc, 0.04 mole) HCl was added to 200 cc $H_2O$ and the resulting solution was added slowly to the receiver. At first, the pot temperature rose to 30°–35° C. and rapidly subsided. The rest of the HCl solution was added. The ice bath was removed; 2 phases formed: a clear upper $H_2O$ and light brown viscous lower oil layer. 100 cc $CHCl_3$ were added to the pot to dissolve the oil, and the whole was transferred to a 1 liter separatory funnel; 100 ml additional $CHCl_3$ were added. Most of the organic layer was decanted. The remaining organic and $H_2O$ layers were washed twice with $CHCl_3$, the resulting organic layers being decanted. The entire combined organic phase was dried over anhydrous $MgSO_4$ overnight. The whole material and a smaller one for product. Cut No. 3: b.p. 140°–145° (.01 mm) showed the major component as product (faster moving component) and a smaller spot for starting sulfone. Cuts 1 and 2 were discarded as they had very little product. All three cuts were solids. Cut No. 3 weighed 5.6 g.

The solid from Cut No. 3 was taken into boiling petroleum ether and filtered to remove cloudiness. The solution was concentrated to about 25 ml and cooled in an ice-water mixture. The solid was pressure filtered under nitrogen to give 2.78 g of white solid, m.p. 78°–81° C. The solid was recrystallized from petroleum ether (about 10–15 ml) (cooled to -15° C.). The solid was filtered with a positive pressure of nitrogen to give 2.21 g of a white crystalline solid, m.p. 79.5°–81.5° C.

The nuclear magnetic spectrum showed that there is a typical 1,4-disubstituted aromatic pattern with a relative intensity of 4 protons, comprising a band centered at 7.75 δ due to the two protons ortho to the SO₂ group and its mirror image centered at 7.47 δ due to the two protons ortho to the tertiary butyl group. A quartet of bands centered at 2.84 δ, relative intensity of one proton, is due to the methine proton. The tertiarybutyl and the single methyl resonances overlap to form a band of relative intensity of 12 protons, the tertiarybutyl resonance appearing as a singlet centered at 1.35 δ and the methyl resonance appearing as a doublet centered at 1.29 δ. There is a singlet at 0.37 δ (37 Hz) flanked by two small satellite doublets with a total relative intensity of 9 protons. This band is due to the trimethyltin group. The two sets of satellite doublets are due to the coupling of the three methyl groups to the two isotopes of Sn — $Sn^{117}$ and $Sn^{119}$ — with a nuclear spin of ½. Thus, the structure as presented in the paragraph preceding this Example is confirmed.

The comparative data in the following table (Table VII) were obtained on trimethylphenylsulfonylethylstannane, a Peterson compound (trimethylphenylsulfonylmethylstannane and the Peterson Hydrolysis product referred to above (trimethyltin hydroxide. The Peterson compound was prepared in accordance with Example 1 of U.S. Pat. No. 3,794,670, except that an equivalent amount of trimethyltin chloride was used instead of trimethyltin bromide. The trimethyltin hydroxide was prepared by the method set forth by J. G. A. Luijten, Rec. trav. chim. 82, 1179 (1963).

The mite one-day residual test differed as follows from that set forth in Example 9. The plants were held in a growth chamber maintained at 85° F., and were exposed to high intensity fluorescent lights for 14 hour days. The recorded observations were made 3 days after loading the mites.

The 3-day tobacco bud worm test on cotton differed as follows from that set forth in Example 10. The plants used were 3 weeks old, and were covered with cheesecloth during the test. Six replicates were used for each test compound, with 1 worm per plant. The plants were infested with larva 3 days after the spray application and the recorded observations were made 6 days after the spray application. In both of these tests, the solutions were made in terms of millimoles/liter so that the results would be strictly comparable, since the compounds are of different molecular weights.

The unsubstituted phenyl compounds were used in this comparative test because it was found that an alkyl-substituted phenyl Peterson compound could not be made by the method of Peterson U.S. Pat. No. 3,794,670. The following details an attempt to prepare trimethyl 4-t-butylphenylsulfonylmethylstannane.

Following the procedure set forth in U.S. Pat. No. 3,794,670 for example 1, 94.0 ml. (0.15 mole) of 1.6M n-butyllithium in n-hexane were added dropwise, with stirring under nitrogen at 0° to 8° C., to a solution of 18.5 ml (0.18 mole) of diethylamine in 50 ml of dry benzene. A solution of 29.8 g (0.15 mole) of trimethyltin chloride in 50 ml of benzene was added to the white suspension at 0°–5° over 40 minutes. The reaction mixture was stirred at room temperature for 1.5 hours. To the reaction mixture were added 31.8 g (0.15 mole) of 4-t-butylphenyl methyl sulfone. After stirring the reaction mixture overnight at room temperature, the flask was heated to distill off diethylamine and benzene and then maintained at 100°–110° C. for 2 hours. After cooling to room temperature, a solution of 4g of concentrated hydrochloric acid in 200 ml of water was added to the reaction mixture with rapid stirring for 2 minutes. The resulting mixture was quickly washed into a separatory funnel with 200 ml of chloroform. The lower organic phase was separated, dried (MgSO₄) and stripped of solvent to give 51.8 g of an amber colored oil. the viscous oil was subjected to vacuum distillation using a short-path distillation head. The following cuts were taken:

Cut No. 1, b.p. 26°–145° C. (5 × 10⁻³–.014 mm), a solid

Cut No. 2, b.p. 145°–158° C. (0.014–0.03mm), an oily solid

Cut No. 3, b.p. 158°–159° C. (0.03–0.48 mm), an oil

The pot residue, a black brittle glass when cooled, weighed 16.2 g. The cuts were analyzed by (glpc) gas-liquid phase chromatography using a 6 feet × ⅛ inch column packed with 10% of silicone gum rubber on silanized diatomaceous earth at a column temperature of 260° C. The main component of Cut No. 1 was shown to be 4-t-butylphenyl methyl sulfone; No. 2 consisted of a mixture of mainly starting sulfone plus a higher boiling component; No. 3 consisted of the same mixture enriched in the higher boiling component. There also was a more volatile component which in- Table VII

| | Mite One-Day Residual % Control (millimoles/liter) | | | Tobacco Bud Worm | | | | | |
|---|---|---|---|---|---|---|---|---|---|
| | | | | % Control (millimoles/liter) | | | % Feeding Reduced (millimoles/liter) | | |
| | 0.6 | 0.3 | 0.15 | 0.6 | 0.3 | 0.15 | 0.6 | 0.3 | 0.15 |
| (CH₃)₃SnCH₂CH₂—S(O)₂—C₆H₅ | 98.4 | 100 | 73 | 100 | 83 | 83 | 98 | 92 | 88 |
| (CH₃)₃SnCH₂—S(O)₂—C₆H₅ | 44 | 14 | 18 | 66 | 0 | 40 | 90 | 52 | 73 |
| (CH₃)₃SnOH | 9 | 34 | 7 | 66 | 16 | 16 | 81 | 69 | 50 |

The decided superiority of the compound having two methylene groups between the Sn and SO₂ moieties over the closest comparable Peterson compound and over the hydrolysis product of the latter is readily apparent.

creased in amount in each successive cut. The latter observation accompanied by a gradual loss in vacuum is usually associated with some thermal decomposition. Cuts No. 2 and No. 3 were combined for a second distillation using a vacuum jacketed vigreaux column. One cut was obtained, b.p. 43°–125° C. (0.016–0.025 mm), a solid which, when analyzed, showed mainly the starting sulfone and little of the higher boiling component. Analysis of the pot residue, 8 g, showed ~1:1 mixture of the starting sulfone and the higher boiling component. The vigreaux column was replaced by a short-path head and a third distillation was run on the pot residue. The following cuts were taken:

Cut No. 1, b.p. 28°–172° (0.002–0.02 mm), about 1 ml of a yellowish liquid

Cut No. 2, b.p. 174°–166° C. (0.025 –0.13 mm), solid, 1.5 ml

Analysis of Cut No. 1 again showed a mixture of the same two components and Cut No. 2 showed only the starting sulfone. A sample of Cut No. 1 was analyzed by nuclear magnetic resonance spectroscopy (NMR). The NMR spectra showed a 1:2 molar mixture of the starting sulfone and the expected product, 4-t-butylphenylsulfonylmethyltrimethylstannane. In summary, the product could only be obtained as a mixture with the starting sulfone despite three distillation attempts to separate the mixture. All evidence points to the thermal instability of the product at the temperature required to distill the starting sulfone. In addition, examination of the cold traps (-70° C.) (used to prevent contamination of the vacuum pump) showed a liquid (stench) which volatilized on reaching room temperature, the volatile material being a decomposition product.

A second attempt to prepare and isolate trimethyl 4-t-butylphenylsulfonylmethylstannane, using the general procedure of Example III in U.S. Pat. no. 3,794,670 and the same starting materials set forth above, was unsuccessful. In this case, 53.6 g of an oil was isolated from the work-up. Using a vacuum jacketed vigreaux column, distillation of the oil gave only a small amount of distillate, b.p. 70°–132° C. (0.02 –0.04 mm) which analyzed as starting sulfone. After replacing the column with a short path head, only 11.9 g of distillate, b.p. 70°–150° C. (0.019 –0.27 mm), could be obtained due to a steady loss of vacuum. Analysis of the distillate by glpc showed the starting sulfone to be at least 90% of the distillate.

While the invention has been described with particularity and in some detail, it should be understood that it is susceptible to various changes and modifications that will occur to those skilled in the art without departing from the scope of the spirit of the invention.

What is claimed is:

1. A tetrasubstituted organotin compound having the formula

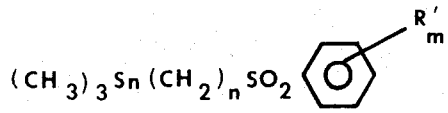

wherein R' is the same or different and is selected from the group consisting of linear and branched alkyl having 1 to 20 carbon atoms, cycloaliphatic having 4 to 6 carbon atoms and straight chain and branched alkenyl having 2 to 20 carbon atoms, $m$ is an integer from 1 to 3 and $n$ is an integer from 2 to 11.

2. The compound of claim 1 wherein said compound is 2-(p-t-butylphenylsulfonyl)ethyltrimethylstannane.

3. The compound of claim 1 wherein said compound is 2-(p-tolylsulfonyl)ethyltrimethylstannane.

4. The compound of claim 1 wherein said compound is 2-(p-cyclohexylphenylsulfonyl)ethyltrimethylstannane.

5. The compound of claim 1 wherein said compound is 6-(p-tolylsulfonyl)hexyltrimethylstannane.

6. The compound of claim 1 wherein said compound is 11-(p-tolylsulfonyl)undecyltrimethylstannane.

7. The compound of claim 1 wherein said compound is 4-(p-t-butylphenylsulfonyl)butyltrimethylstannane.

* * * * *